(12) United States Patent
Matsubara et al.

(10) Patent No.: US 7,384,601 B2
(45) Date of Patent: Jun. 10, 2008

(54) AUTOMATIC ANALYZER

(75) Inventors: Shigeki Matsubara, Hitachinaka (JP);
Yukie Tokiwa, Hitachinaka (JP);
Kyoko Imai, Hitachinaka (JP);
Tomonori Mimura, Tomobe (JP)

(73) Assignee: Hitachi High-Technologies Corporation, Tokyo (JP)

( * ) Notice: Subject to any disclaimer, the term of this patent is extended or adjusted under 35 U.S.C. 154(b) by 194 days.

(21) Appl. No.: 10/603,624

(22) Filed: Jun. 26, 2003

(65) Prior Publication Data
US 2005/0175506 A1 Aug. 11, 2005

(30) Foreign Application Priority Data
Jun. 28, 2002 (JP) .............................. 2002-189015

(51) Int. Cl.
*G01N 33/48* (2006.01)
(52) U.S. Cl. .......................................... 422/67; 422/62
(58) Field of Classification Search .................. 422/65, 422/63, 67, 62
See application file for complete search history.

(56) References Cited

U.S. PATENT DOCUMENTS

| 4,873,633 | A | * | 10/1989 | Mezei et al. .................. 356/39 |
| 4,901,221 | A | * | 2/1990 | Kodosky et al. ............. 715/771 |
| 5,314,825 | A | | 5/1994 | Weyrauch et al. |
| 5,576,946 | A | * | 11/1996 | Bender et al. ................. 700/17 |
| 6,080,364 | A | * | 6/2000 | Mimura et al. ............... 422/67 |

FOREIGN PATENT DOCUMENTS

| EP | 0359049 | * | 3/1990 |
| EP | 0732591 | * | 9/1996 |
| EP | 0871034 | * | 10/1998 |
| EP | 0952452 | * | 10/1999 |
| EP | 1061372 | | 12/2000 |
| JP | 8-101204 | | 4/1996 |
| JP | 9-211003 | | 8/1997 |

* cited by examiner

*Primary Examiner*—Jill Warden
*Assistant Examiner*—Natalia Levkovich
(74) *Attorney, Agent, or Firm*—Mattingly, Stanger, Malur & Brundidge, P.C.

(57) ABSTRACT

In an automatic analyzer, necessary setup works are displayed prior to analysis operation. The present invention can realize an automatic analyzer which can be used by an inexperienced operator to execute all necessary setup works. A maintenance button, data erase button, reagent status button, reagent prime button, calibration button and QC button are displayed on a system viewing screen displayed on an operation part. The display colors of the maintenance button or the like are changed (for example, the display color is changed to red, yellow or the like) in response to the status of the automatic analyzer in order to recognize necessary setup works prior to analysis operation for an operator.

8 Claims, 6 Drawing Sheets

AUTOMATIC ANALYZER

BACKGROUND OF THE INVENTION

1. Field of the Invention

This invention relates to an automatic analyzer for automatically analyzing samples to determine, the concentrations or the like of specific components in the samples, and especially to an automatic analyzer which even for an operator inexperienced in its operation, permits fail-free operation by performing necessary operation upon startup or the like of the analyzer.

2. Description of the Related Art

Analyses of biological samples collected from patients, such as blood and urine, are widely performed to diagnose their morbidities, and therefore, automated analyzers are used in hospitals and clinical laboratories.

Prior to operations for an analysis, such an automatic analyzer, in many instances, requires a variety of setup or preparation work such as various maintenance work, reagent replacements, reagent replenishments, calibrations, quality control and the like. It is, however, very irksome to perform all of these setup or preparation work, and even for an operator skilled in the operation of the analyzer, a substantial time is needed to check and perform such setup or preparation work in their entirety. When an operator inexperienced in the operation of the analyzer performs these setup or preparation work for night duty or the like, inadvertent omission of necessary work may occur, thereby requiring setup or preparation work again or causing a reduction in the reliability of measurement data.

JP-A-8-101204 discloses an analyzer which displays, on screens, flow diagrams of operations required for starting up the analyzer. A start-up of the analyzer in accordance with instructions on the screens makes it possible to preset data, which are required for a desired analysis and processing, by simple operations.

SUMMARY OF THE INVENTION

In JP-A-8-101204, all the screens are successively shown in a fixed order upon presetting data required for a desired analysis and processing even when one or more of the screens require no particular inputs or changes because of the status of the analyzer. In other words, an operator is required to go through the procedure at a time of a start-up of the analyzer by successively displaying all the screens even when one or more of these screens require no particular inputs or changes. A substantial time may, therefore, be required for the start-up, although no error arises insofar as all the setup operations are performed in accordance with the instructions on the screens. In such a case, the time required for the set-up of the analyzer can be shortened provided that setup operation steps, performance of which is required upon starting up the analyzer, are clearly indicated.

An object of the present invention is to provide an automatic analyzer which allows even an operator, who is inexperienced in its operation, to perform required setup work beforehand without omission in a short time by displaying necessary operations on screens prior to operations for an analysis while reflecting the status of the analyzer at that time. The present invention also has, as another object, the provision of an automated analysis system with plural analysis units connected to a transport line, which displays each analysis unit, which requires setup operations, differently, for example, in a different color to permit performance of setup operations for the analysis unit without failure To achieve the above-described objects, the present invention provides the following automatic analyzer and automated analysis system.

In one aspect of the present invention, there is thus provided an automatic analyzer for automatically analyzing samples to obtain their data of analysis items. The automatic analyzer includes a means for displaying a flow of setup procedure, which is required for starting up the automatic analyzer, as plural procedure steps upon start-up of the automatic analyzer. The display means is provided with a function to display at least one of the procedure steps, said at least one procedure step requiring an operation at a time of the start-up, differently from the remaining steps each of which requires no operation at the time of the start-up.

In another aspect of the present invention, there is also provided an automated analysis system for placing samples, which are to be analyzed, in a sample rack, transporting via a transport line the rack with the samples placed thereon from a sample rack loading section to an analysis unit connected to the transport line, and performing analyses of the samples. The automated analysis system includes a means for displaying, on the same screen, a procedure step display section showing a flow of setup procedure, which is required for starting up the automated analysis system, as plural procedure steps and a configuration display section showing configuration of the automated analysis system upon start-up of the automated analysis system. The display means is provided with a function such that, when the procedure steps includes at least one procedure step which requires an operation at a time of the start-up, said at least one procedure step requiring the operation is shown in the procedure step display section differently from the remaining steps each of which requires no operation at the time of the start-up and a unit associated with the at least one procedure step requiring the operation is shown in the configuration display section differently from units associated with the remaining steps each of which requires no operation at the time of the start-up.

DETAILED DESCRIPTION OF EMBODIMENTS OF THE INVENTION

Referring to the drawings, a description will hereinafter be made about the specific embodiment of the present invention.

Figure 1:
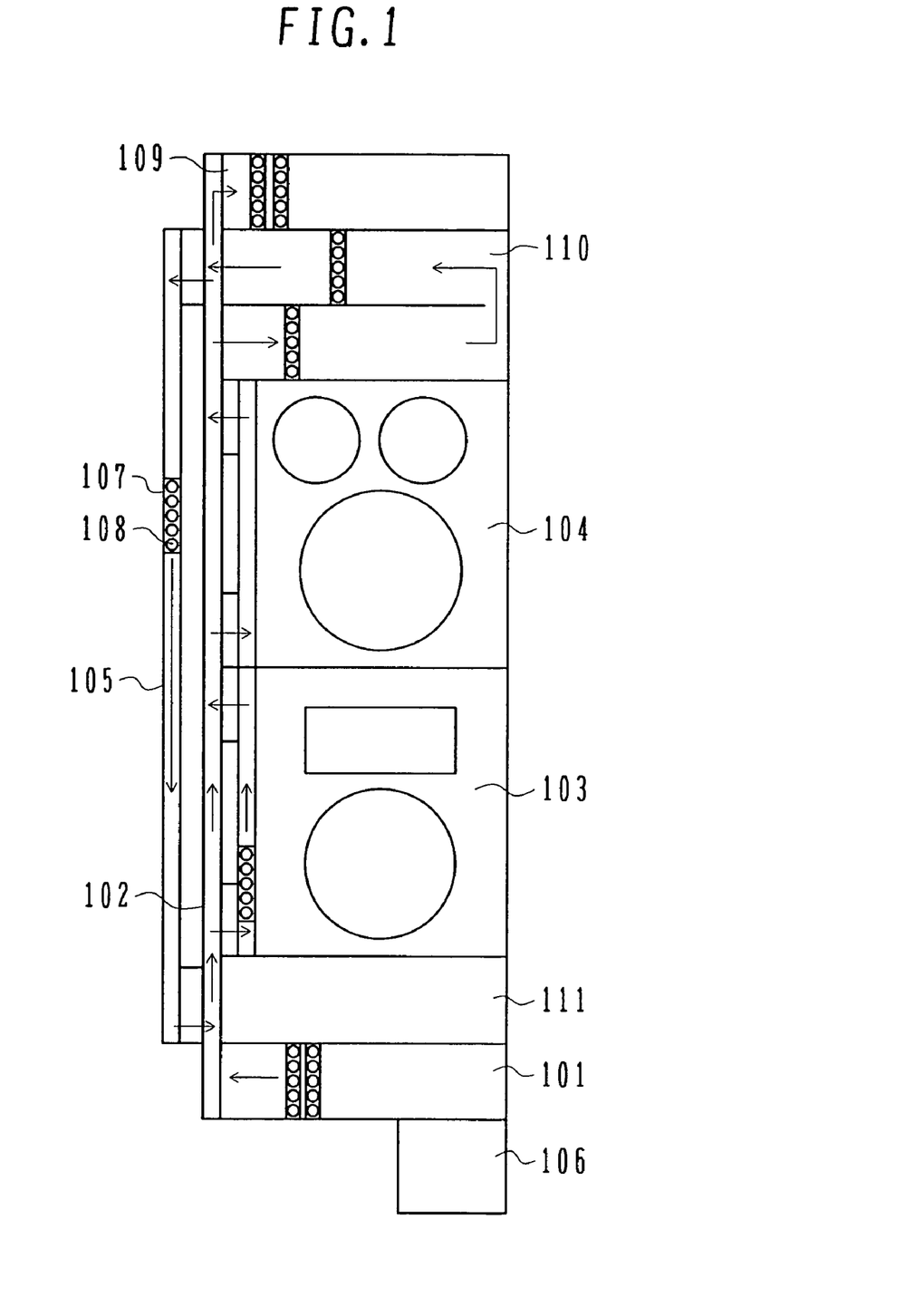
FIG. 1 is an overall schematic construction diagram of an embodiment of an automatic analyzer according to the present invention.

FIG. 1 is an overall schematic construction diagram of an embodiment of an automatic analyzer according to the present invention.

In FIG. 1, a transport line 102 is arranged to convey a rack 107, in which plural sample vessels 108 can be placed, from a sample loading section 101 where a plurality of such racks can be loaded. Adjacent to the transport line 102, a first analysis unit (immunoassay unit) 103 and a second analysis unit (biochemical analysis unit) 104 are disposed, and a sample storage section 109 is disposed at a downstream end. In addition to the transport line 102, a waiting buffer (1)110 to wait the determination to determine whether the sample is to be retested or not before each rack 107 with at least one sample vessel 108 carried therein is conveyed to the next analysis unit or the sample storage section 109 and an electrolyte analysis unit 111 are arranged. A re-testing transport part 105 is also arranged to transport the rack 107 to an analysis unit from the waiting buffer (1)110 when the sample is determined to be retested. An operating unit 106 is also connected to perform operations of the individual units. The first analysis unit 103 and the second analysis unit 104 are provided with sample dispensing mechanisms, respectively, and the transport line 102 conveys the sample vessels 108, which are placed in the rack 107, to sample aspirating positions in the individual analysis units.

A description will next be made of flows of processing in the automatic analyzer. In the embodiment of FIG. 1, each rack 107 which has been loaded in the sample loading section 101 for conveyance on the transport line 102 is conveyed firstly to the sample aspirating position in the first analysis unit 103. Subsequent to completion of aspiration of samples from the individual sample vessels 108 in the rack 107 into the first analysis unit 103, the rack 107 is conveyed to the second analysis unit 104. In this embodiment, the first analysis unit 103 and the second analysis unit 104 are constructed to perform biochemical analyses and immunoassays, respectively, by way of example.

Figure 2:
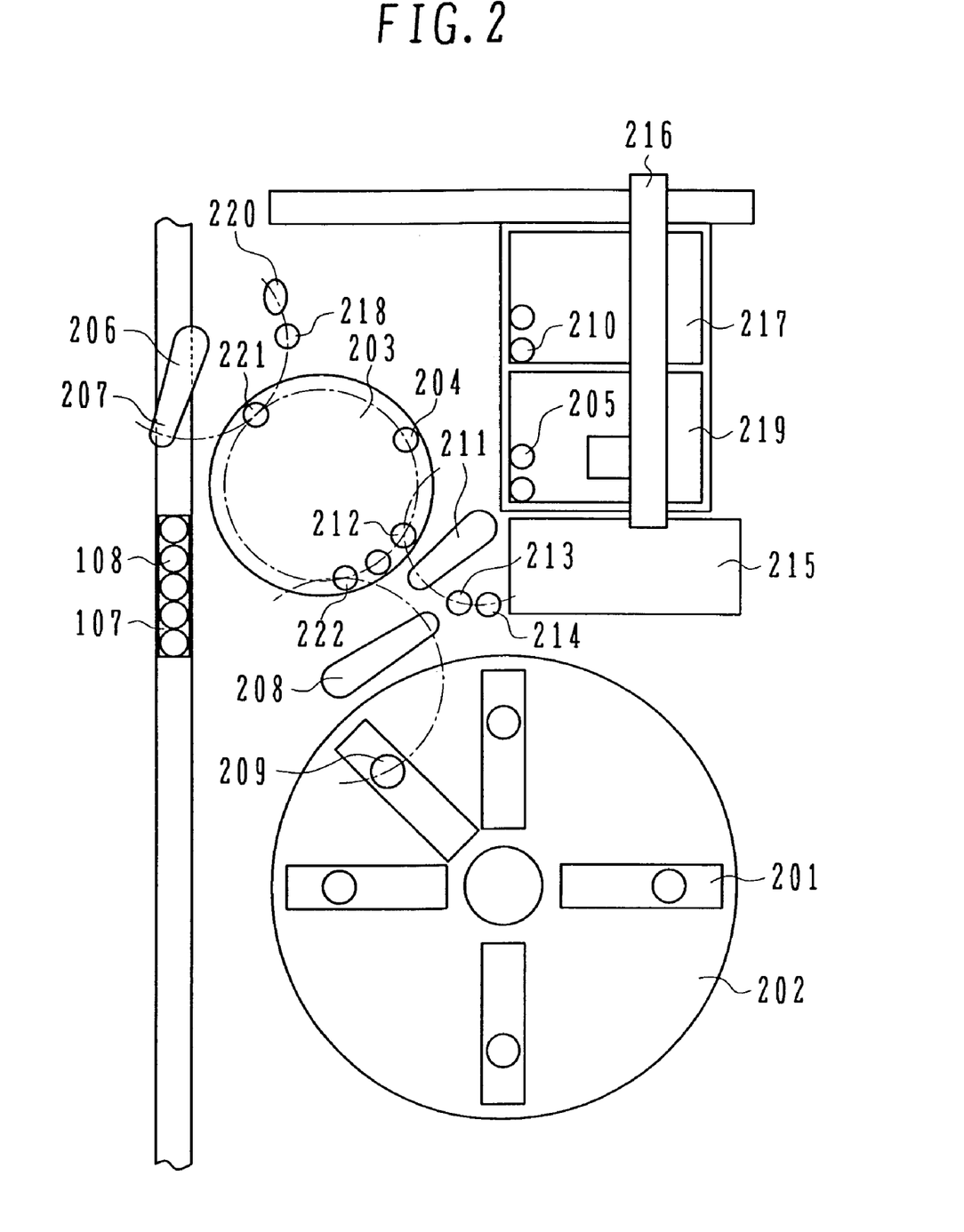
FIG. 2 is a schematic construction diagram of an immunoassay unit in the embodiment of the automatic analyzer according to the present invention.

With reference to FIG. 2, the construction of the immunoassay unit 103 will be described. In FIG. 2, plural reagent vessels 201 are arranged on a reagent disk 202 which can be driven for rotation by a motor. A thermostat tank 203 can be driven for rotation by a motor. Arranged on the thermostat tank 203 are plural reaction positions, in which reaction vessels 205 are accommodated, respectively. Through rotation, the thermostat tank 203 transfers each reaction vessel 205 from a reaction vessel arranging position 204 to a sample injecting position 221, a reagent injecting position 222 and a reaction mixture aspirating position 212. A sample pipetter 206 is movable by a motor from a position above a sample aspirating position 207 to a position above the sample injecting position 221 and vice versa, and is also movable vertically at the respective positions. Upon aspirating the sample, a disposable tip 210 is fitted on a nozzle tip of the sample pipetter 206. A reagent pipetter 208 is movable by a motor from a position above a reagent aspirating position 209 to a position above the reagent injecting position 222 and vice versa, and is also movable vertically at the respective positions. A shipper 211 is movable as desired by a motor over a position above the reaction mixture aspirating position 212, a position above a buffer aspirating position 213 and a position above a flow-cell interior washing solution aspirating position 214, and is also movable vertically at the respective positions. The shipper 211 is also equipped with a function to feed the reaction mixture to a flow cell inside a detector unit 215 via a tube. A tip and reaction vessel transfer mechanism 216 transfers the disposable tip 210 from a tip holding position 217 to a tip fitting position 218 and also, the reaction vessel 205 from a reaction vessel holding position 219 to the reaction vessel arranging position 204. The reagent pipetter 208 and shipper 211 can be washed at outer nozzle walls thereof with water at washing positions (not shown), respectively.

A description will next be made of a flow of processing in the immunoassay unit 103. Firstly, the tip and reaction vessel transfer mechanism 216 transfers the disposable tip 210 to the tip fitting position 218 and the reaction vessel 205 to the reaction vessel arranging position 204. The rack 107 with the sample vessels 108 placed therein is conveyed on the transport line 102 such that the sample vessel 108 containing therein the sample, which is analyzed, comes to the sample aspirating position 207. At the same time, the reagent disk 202 rotates such that the reagent vessel 201 containing therein the reagent for use in the analysis comes to the reagent aspirating position 209. Concurrently with this, the pipetter 206 is fitted with the disposable tip 210 and then, moves to the position above the reagent aspirating position 209. At the reagent aspirating position 209, the pipetter 206 descends to suck the reagent. The pipetter 206 then ascends, and moves toward a pipetter washing position. When the pipetter 206 comes to a position above the pipetter washing position, washing water is sprayed from the pipetter washing position to wash a tip of the disposable tip 210. The pipetter 206 next moves to the position above the sample aspirating position 207. At the sample sucking position 207, the pipetter 206 descends and sucks the sample. Subsequent to the sucking, the pipetter 208 ascends, and moves to a position above the reaction vessel mounting position 204. At the reaction vessel mounting position 204, the pipetter 206 descends, and delivers a mixture of the sample and the reagent into the reaction vessel 205. Subsequent to the delivery, the pipetter 206 ascends and moves to a tip discarding position 220. When the pipetter 206 comes to the tip discarding position 220, the pipetter 206 discards the disposable tip 210.

After a time suited for a reaction has elapsed, the shipper 211 moves to the position above the buffer aspirating position 213. At the buffer aspirating position 213, the shipper 211 descends and sucks a buffer. Subsequently, a tip portion of the shipper is washed at the shipper washing position.

Next, the tip and reaction vessel transfer mechanism 216 next transfers the reaction vessel 205 from the reaction vessel arranging position 204 to the reaction mixture aspirating position 212. At the reaction mixture sucking position 212, the shipper 211 sucks the reaction mixture. Subsequent to the sucking of the reaction mixture, the shipper 211 moves to the buffer aspirating position 213 and sucks the buffer. The buffer and the reaction mixture are fed in combination into the flow cell inside the detector unit 215 through a tube, and a measurement is performed. At the flow-cell interior washing solution sucking position 214, the shipper 211 sucks a flow-cell interior washing solution, and washes the interior of the flow cell inside the detector unit 215 through the tube.

Figure 3:
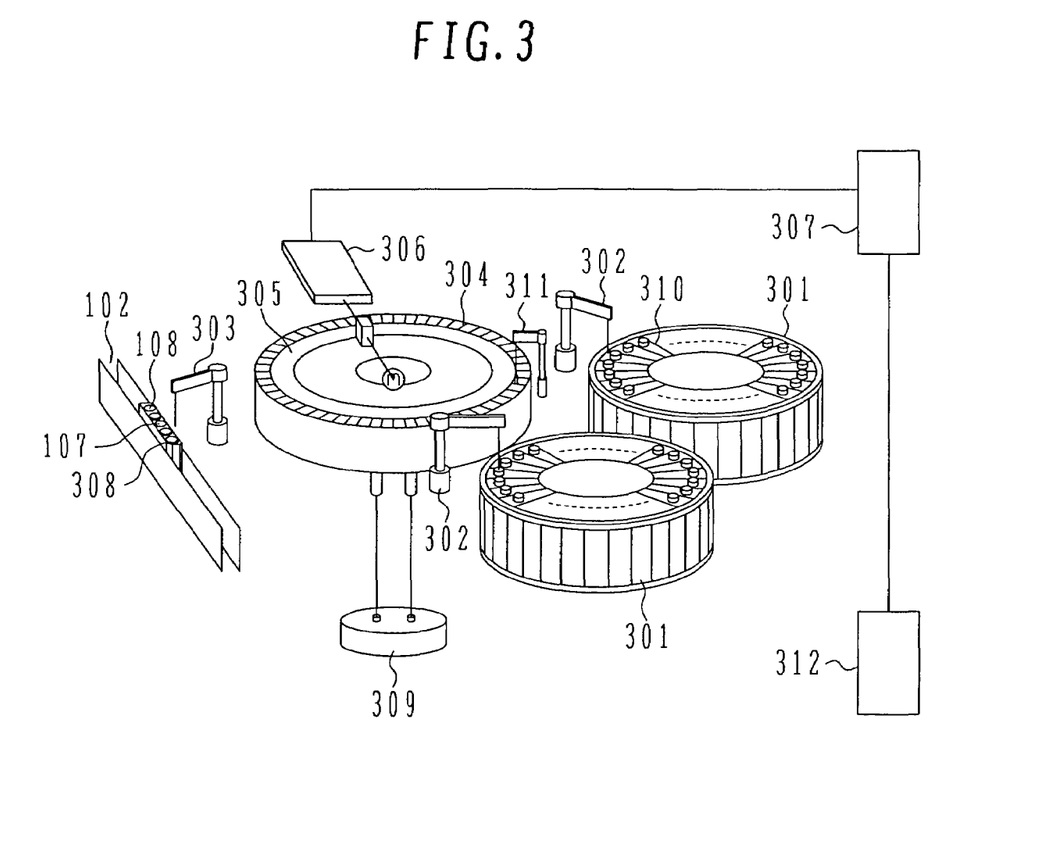
FIG. 3 is a schematic construction diagram of a biochemical analysis unit in the embodiment of the automatic analyzer according to the present invention.

Referring next to FIG. 3, a description will be made of the construction of the biochemical analysis unit 104. In FIG. 3, the biochemical analysis unit 104 is composed of a reagent system equipped with reagent disks 301 as reagent vessel holding positions and reagent pipetters 302, a sample system equipped with a sample pipetter 303, a reaction system equipped with a reaction disk 305 which includes reaction vessels 304, and a measurement system equipped with a multi-wavelength photometer 306 and an analog/digital converter 307.

In FIG. 3, the rack 107 with the sample vessels 108 placed therein is conveyed on the transport line 102 to a sample aspirating position 308. The sample pipetter 303 sucks the sample from each sample vessel 108, and injects a predetermined amount of the sample into the reaction vessel 304.

The reaction vessel 304 with the sample injected therein is moved to a first reagent adding position through a reaction disk 305 arranged in communication with a thermostat tank 309. At this time, the reagent disk 301 which carries therein a reagent vessel 310 corresponding to the current analysis item is rotated such that the reagent vessel 310 is located below the corresponding reagent pipetter 302 held on a lift arm, and after that, the reagent pipetter 302 descends to suck a first reagent from the reagent vessel 310. Into the reaction vessel 304 moved to the first reagent adding position, the first reagent sucked in the reagent pipetter 302 is added to a predetermined amount. After the addition of the first reagent, the reaction vessel 304 is moved to the position of a stirrer 311, and first stirring is performed.

A beam of light generated from a light source is caused to pass through the reaction vessel 304 the contents of which have been stirred, and is allowed to enter the multi-wavelength photometer 306. An absorbance of the reaction mixture as the contents of the reaction vessel 304 is then detected by the multi-wavelength photometer 306. A signal which corresponds to the absorbance so detected is supplied to a computer 312 via the analog/digital (A/D) converter 307 and an interface (not shown), and is converted into a concentration of an analysis object or a test object, in a measurement target in the sample.

Subsequent to completion of the measurement, the reaction vessel 304 is moved to the position of a washing vessel washing mechanism. After the internal reaction mixture is discharged at a washing position by the reaction vessel washing mechanism, the reaction vessel 304 is washed with water and is provided for use in a next analysis.

Figure 4:
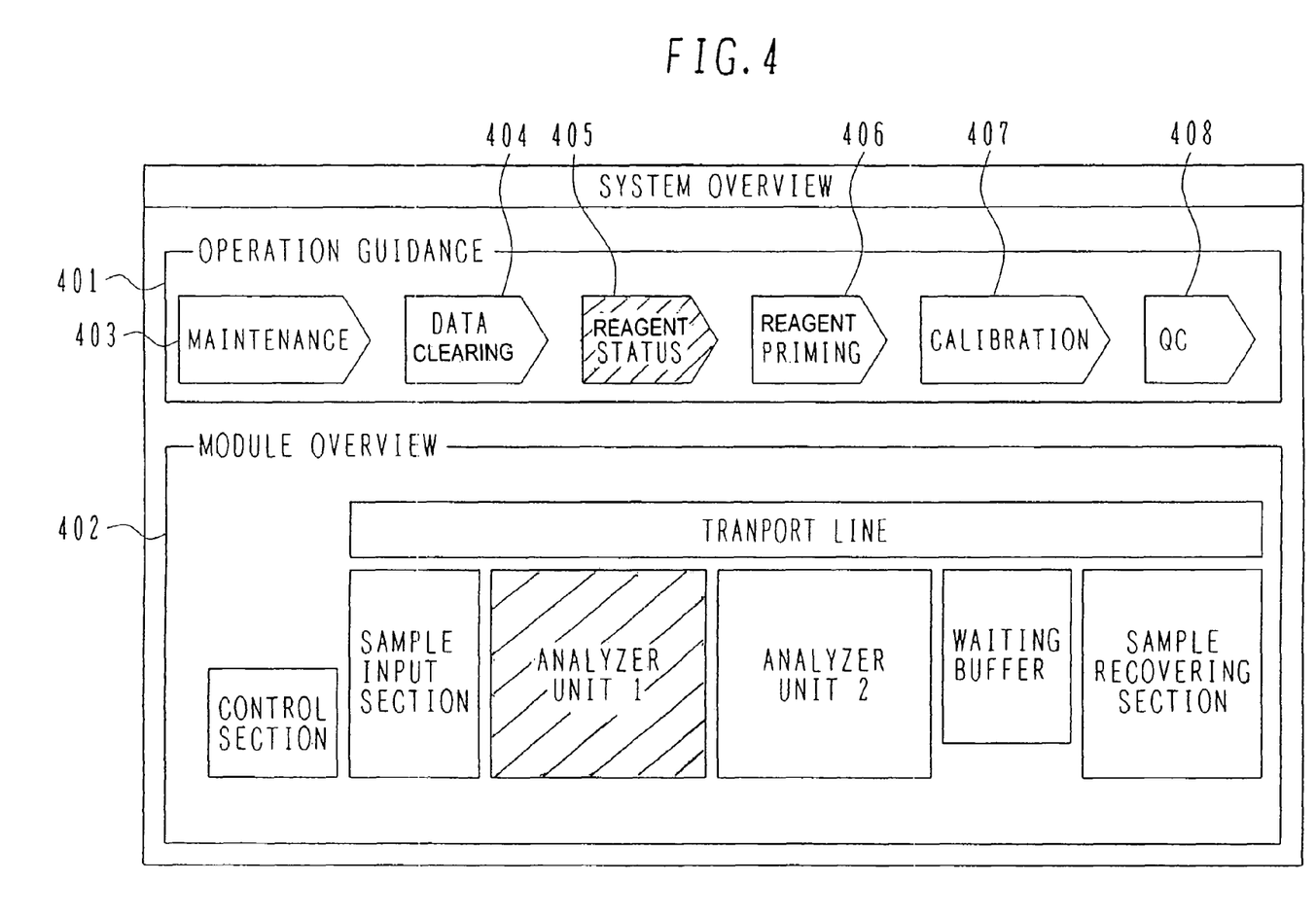
FIG. 4 is a system overview screen of the embodiment of the automatic analyzer according to the present invention.

A description will next be made of flows of analysis and processing operations by the automatic analyzer. As soon as a power switch of the analyzer is turned on by an operator, the analyzer automatically initiates setup operations. In the setup operations, position resetting operations of the mechanism systems, degassing operations of individual flow paths, and the like are performed. Subsequent to completion of the setup operations, the analyzer is in a standby state, and the operator performs setup work required for performing analyses on that day. Upon performing the setup work, the operator proceeds with operations with reference to a system overview screen shown on the display in the operating unit 106. Referring to FIG. 4, the system overview screen is composed of two sections, that is, an operation guidance section 401 and a module overview section 402. In the operation guidance section 401 of the system overview screen, buttons are arranged including a maintenance button 403, a data clear button 404, a reagent status button 405, a reagent priming button 406, a correction or calibration button 407, and a QC button 408. Depending on information such as the execution status of maintenance and the current residual amounts of loaded reagents, the display colors of these buttons are changed. The operator proceeds with pre-analysis setup work on the basis of their color information. A description will hereinafter be made about specific functions and display colors of the individual buttons.

Maintenance Button 403

Figure 5:
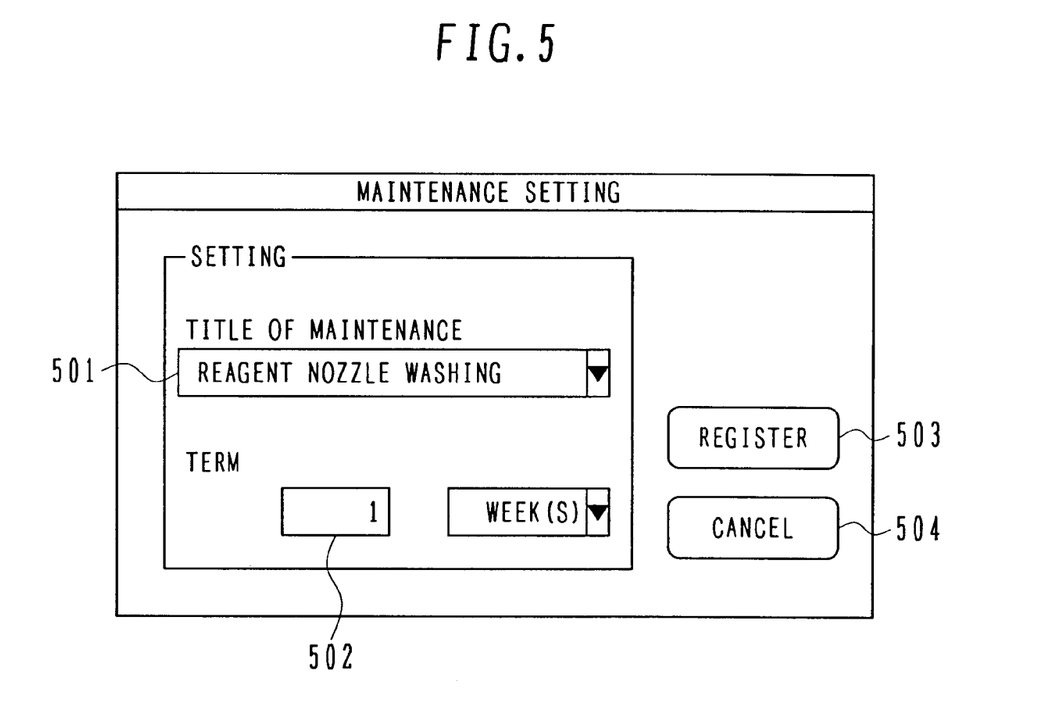
FIG. 5 is a maintenance item duration setting screen of the embodiment of the automatic analyzer according to the present invention.

The maintenance button 403 is displayed in yellow or red when there is at least one maintenance item left unexecuted for days beyond its corresponding duration from its preceding execution on the basis of information on durations preset for the individual maintenance items. With reference to the duration setting screen of FIG. 5, a description will next be made about the setting of durations for the maintenance items. On the screen, the operator can select any desired one of the maintenance items from a maintenance title list box 501, and with respect to the maintenance item, can set a duration in days, weeks or months in a duration input box 502. Subsequent to the setting of the duration, depression of a register button 503 results in registration of the setting whereas depression of a cancel button 504 leads to cancellation of the setting.

Reagent Status Button 405

Figure 6:
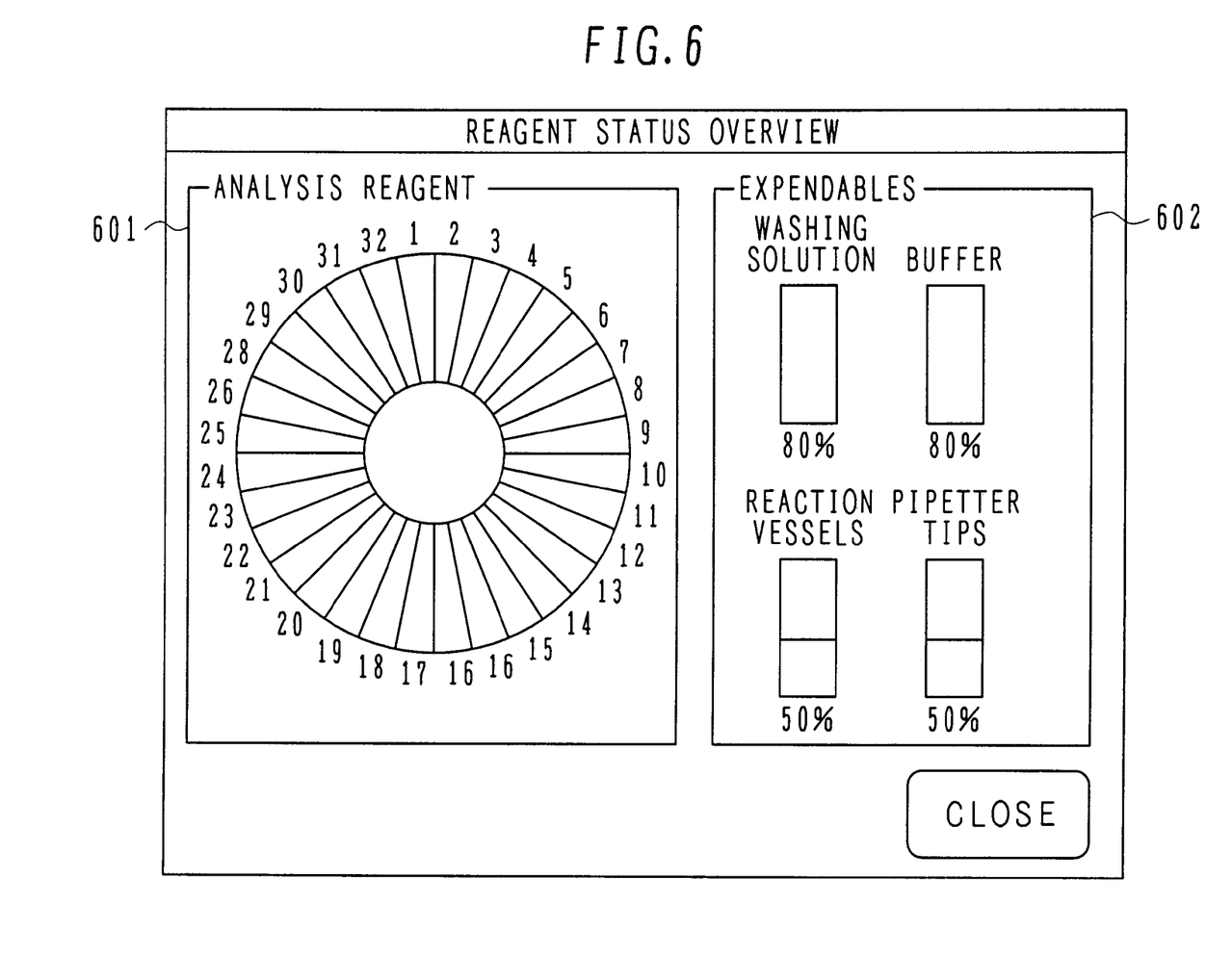
FIG. 6 is a reagent status overview screen of the embodiment of the automatic analyzer according to the present invention.

The reagent status button 405 is displayed in red when the current residual amount of the reagent for at least one of the analysis items is determined to be zero (0) on the basis of the data base of information on the reagents loaded on the analyzer. On the other hand, the reagent status button 405 is displayed in yellow or purple when the current residual amount of the reagent for at least one of the analysis items is determined to be smaller than its corresponding residual amount preset for the display of a warning. The reagent status overview screen of FIG. 6 is composed of an analysis reagent information display section 601 and an expendables information display section 602. The analysis reagent information display section 601 shows the reagent disk 202 or one of the two reagent disks 301 in the corresponding actual analysis unit as looked down upon from above, and discriminates the status of each reagent vessel by its display color in such a way that the corresponding sector is displayed in red when the residual amount is 0 or in yellow when the residual amount is not greater than a specified value. The expendables information display section 602, on the other hand, shows residual amounts of the expendables used in the individual analysis units, and discriminates the status of each expendable by its display color in such a way that the corresponding box is displayed in red when the residual amount of the expendable is zero (0) or in yellow when the residual amount of the expendable is not greater than a specified value.

Reagent Priming Button 406

The reagent priming button 406 is displayed in red when at least one of newly arranged reagent vessels is determined to still remain unprimed on the basis of the data base of the information on the reagents currently arranged on the analyzer.

Calibration Button 407

The calibration button 407 is displayed in yellow or red when at least one of reagents currently arranged on the analyzer is determined to have been subjected to no calibration or to have been arranged there beyond the duration of its calibration on the basis of the data base of the information on the reagents currently loaded on the analyzer.

The conception of "calibration" is included in the conception of "correction".

QC Button 408

The QC button 408 is displayed in yellow or red when at least one of reagents currently arranged on the analyzer is determined to require a comparison with its corresponding quality control sample on the basis of the data base of the information on the reagents currently arranged on the analyzer.

In accordance with the operation guidance in the system overview screen, the operator performs setup work with respect to matters, which are displayed in red, yellow or purple, successively rightwards from one displayed on a left side of the screen.

When the analysis units 1 and 2 and the like shown in the module overview section 402 include one or more units or the like to be subjected to a setup operation upon displaying these buttons in different colors, the one or more units or the like can be displayed in different color or colors while displaying the buttons in the different colors. When the colors of the reagent status button 405 and analysis unit 1 have been changed as shown by the cross hatching in FIG. 4, for example, the operator can recognize at a first glance that a reagent-related setup operation such as a reagent replacement is needed for the analysis unit 1. This makes it possible to shorten the time required for setup work or the like upon starting up the analyzer. When plural analysis units are connected to a transport line or when the operation guidance section 401 includes one or more buttons which have not been changed in color, the above-described function allows the operator to recognize that setup operations corresponding to the one or more buttons are unnecessary (in other words, are not essential). The setup operations corresponding to the one or more buttons can, therefore, be skipped without needing confirmation of their details by depressing the one or more buttons.

According to the present invention, even an operator inexperienced in the operation of the automatic analyzer or automated analysis system can surely perform setup work, which is required for an analysis operation, by proceeding with the setup work in accordance with the at least one operation step differently displayed by the display means, for example, by relying upon color indications of individual buttons in an operation guidance section displayed on a system overview screen in an analysis operating unit and successively proceeding with setup work for an analysis operation in accordance with the button instructions from a left side to a right side on the screen.

What is claimed is:

1. An automatic analyzer for automatically analyzing samples, comprising:
   a sample loading section for loading sample racks containing sample holding vessels having samples therein;
   analysis units for analyzing said samples;
   transport lines for transporting said sample racks from said sample loading section to said analysis units;
   reaction vessels in said analysis units for reacting samples and reagents;
   a display section configured to display on a screen images of a flow of plural setup operation steps used for starting up said automatic analyzer, said display section further displaying images of analysis units on the same screen of said automatic analyzer; and
   a control section configured to control said display section to display the images of setup operation step or steps requiring a setup operation by an operator with a displaying manner different from a displaying manner of an image of another setup operation step or steps not requiring a setup operation by an operator, and to control said display section to display an image of an analysis unit requiring said setup operation by an operator with a said displaying manner different from an image of a displaying manner of analysis units not requiring setup operation by an operator, but in the same manner as the images of the setup operation step or steps.

2. An automatic analyzer according to claim 1, wherein said operation steps comprise at least one operation step selected from the group consisting of maintenance operation of said analyzer, clearing operation of data, preparation operation of reagents to be used in analyses, setup operation of flow paths for said reagents to be used in said analyses, correction operation of individual analysis items, and quality control operation of the individual analysis items.

3. An automatic analyzer according to claim 2, wherein, said maintenance operation of said analyzer is an operation step for managing an execution history of maintenance items of said automatic analyzer, and said display means is configured such that, when there is a maintenance item left unexecuted beyond a predetermined number of days, a box which indicates said operation step for said maintenance of said analyzer is displayed in a different color from other operation steps.

4. An automatic analyzer according to claim 2, wherein, said clearing operation of data is a step for clearing up past garbage data by an operator, and said display means is configured such that, when there is garbage data to be cleared up, a box which indicates said operation step for said clearing of said data is displayed in a different color from other operation steps.

5. An automatic analyzer according to claim 2, wherein said preparation operation of reagents to be used in analyses is an operation step for setting amounts of said reagents required to perform said analyses, said display means is configured such that, when there is an analysis item with respect to which the corresponding reagent is expected to become insufficient for performance, a box which indicates said operation step for said preparation operation of said reagents to be used in said analyses is displayed in a different color from other operation steps.

6. An automatic analyzer according to claim 2, wherein said setup operation of flow paths for reagents is an operation step for washing a flow path for a replaced reagent and priming a replacing reagent.

7. An automatic analyzer according to claim 2, wherein said correction operation of individual analysis items is calibration of said individual analysis items, and said display means is provided with a configured such that, when there is an analysis item which requires execution of calibration, a box which indicates said operation step of correction of said individual analysis items is displayed in a different color from other analysis items.

8. An automatic analyzer according to claim 2, wherein one of said operation steps is a quality control operation of said individual analysis items, and said display means is configured such that, when there is an analysis item which requires execution of a quality control operation, a box which indicates said operation step of a quality control operation of said individual analysis items is displayed in a different color from other analysis items.

* * * * *